United States Patent [19]

Seagro, Jr.

[11] Patent Number: 5,448,074
[45] Date of Patent: Sep. 5, 1995

[54] COLOR REGION ANALYZER FOR DETECTING AND SEPARATING POLYVINYL CHLORIDE FROM POLYETHYLENE TEREPHTHALATE

[76] Inventor: Thomas R. Seagro, Jr., P.O. Box 1609, Cambridge, Ohio 43725

[21] Appl. No.: 156,234

[22] Filed: Nov. 22, 1993

[51] Int. Cl.⁶ .......................................... G01N 21/64
[52] U.S. Cl. .............................. 250/461.1; 209/577; 209/578
[58] Field of Search .............. 356/402, 414, 416, 418, 356/419; 209/580, 581, 582, 522, 524, 577, 578, 580, 581, 582; 250/461.1

[56] References Cited

U.S. PATENT DOCUMENTS

| | | | |
|---|---|---|---|
| 4,278,538 | 7/1981 | Lawrence et al. | 209/581 |
| 5,120,768 | 6/1992 | Sisson | 521/46.5 |
| 5,141,110 | 8/1992 | Trischan et al. | 356/240 |
| 5,252,614 | 10/1993 | Sisson | 521/46.5 |

Primary Examiner—F. L. Evans

[57] ABSTRACT

An apparatus used for quality control in the plastics recycling industry for quality control of recycled post consumer clear plastics beverage containers by their ultraviolet black light reflected color, and sends information to a personal computer connected by analog to digital port that compiles a report by software in the P.V.C. contaminants content of a grain sized probe sample of ground P.E.T. material. The apparatus has a photomultiplier tube fitted with a filter capable of blocking the nanometer light wavelength region reflected ultraviolet black light color of P.E.T., allowing the reflected color of P.V.C. to pass through the filter to allow detection and removal of the P.V.C.. The apparatus is able to detect and remove material that is not within a predetermined nanometer region of reflected ultraviolet black light stimulated color, and by computer software generate a report by analyzing analog to digital logic circuit data on the color region content value of the test sample, The apparatus is useful in determining the amount of contaminants in random samples of clear plastic ground containers.

7 Claims, 8 Drawing Sheets

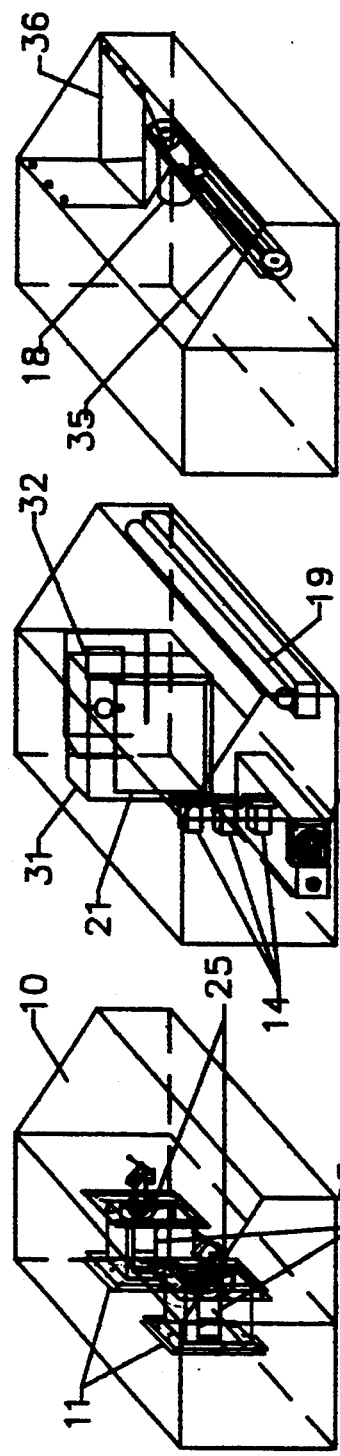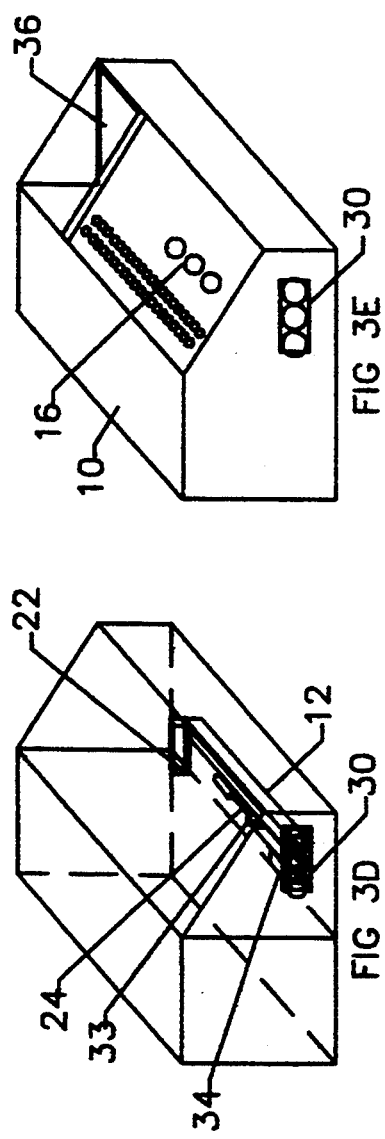

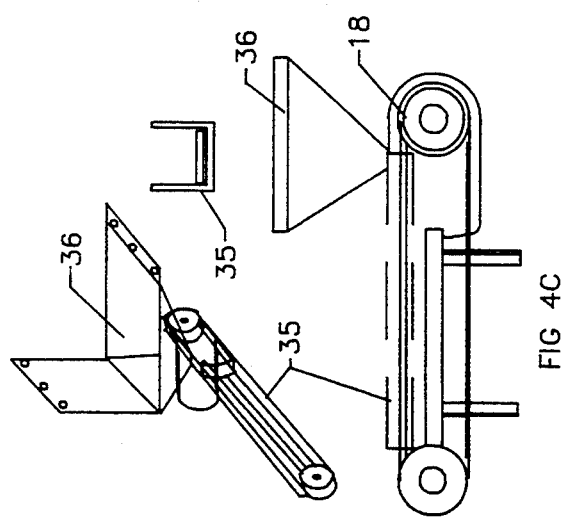
FIG 4C
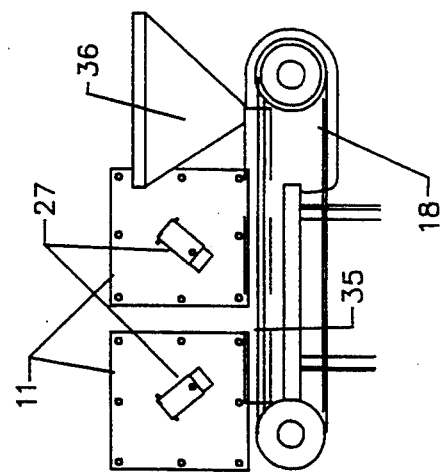
FIG 4B
FIG 4E
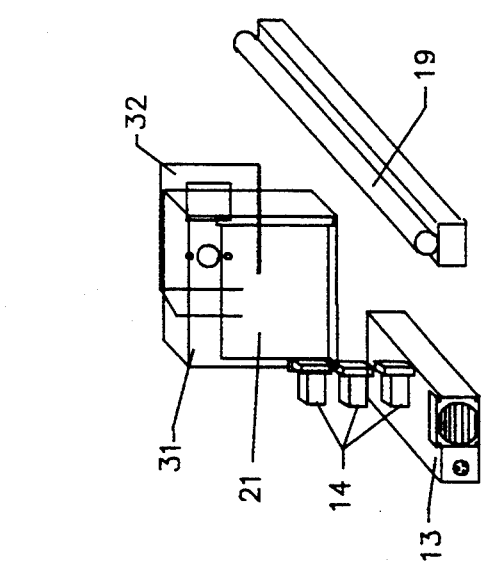
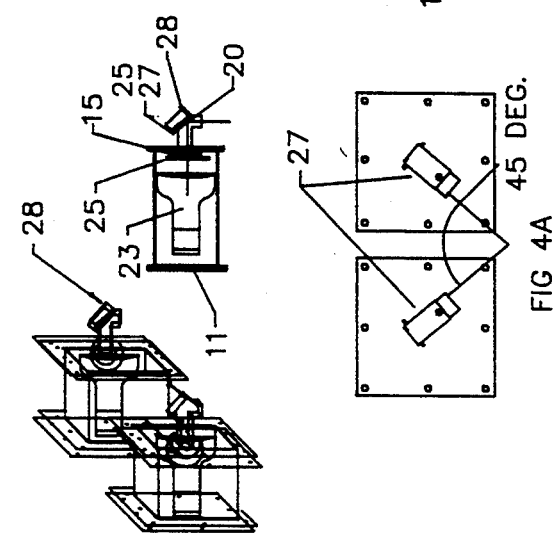
FIG 4A
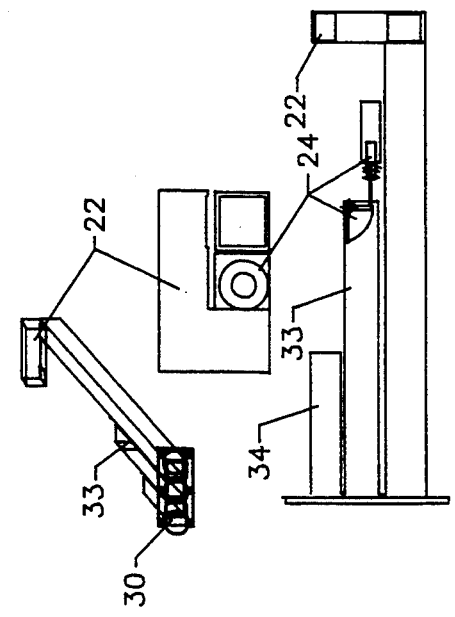
FIG 4D

COLOR REGION ANALYZER FOR DETECTING AND SEPARATING POLYVINYL CHLORIDE FROM POLYETHYLENE TEREPHTHALATE

BACKGROUND

1. Field of Invention

This Invention relates to the Plastic Recycling Industry for quality control in detection of clear polyvinyl chloride (P.V.C.), bottles ground with clear polyethylene terephthalate, (P.E.T.), bottles.

2. Description of Prior Art

P.E.T. (polyethylene terephthalate) as clear plastic containers.

P.V.C. (polyvinyl chloride) as clear plastic containers.

Both materials are post consumer, curb side recycled products.

To my knowledge, except for visual inspection under ultra violet black light and dying the material in question with a solvent to etch the P.V.C. with dye and then visual counting the dyed chips by hand, done only as a means of rejecting entire loads of material if any P.V.C. is found. To this date there has been no method to detect and remove P.V.C. grinds from P.E.T. grinds. I have been advised that the two products being accidently ground together is the greatest problem in the plastics recycling program.

A single P.V.C. bottle in a 1000 lb Gaylord box results in approximately 350 parts per million of contamination, the accepted level is 0 parts per million. If the material goes undetected and is subjected to the process temperature of P.E.T. it turns black and can release toxic fumes that have paralyzed people.

Until now no one has developed a method to detect and remove the P.V.C. contaminant. Contaminated material can not be used for its first intended purpose.

The apparatus I wish to protect by patent and bring to market does and will lead to equipment that will allow the detection and removal of P.V.C. from P.E.T., in grind and whole bottle separation, it is not an expensive process and no additives or harmful radiation are needed.

In March of 1993 as stated in Disclosure Document No. 341610 filed Oct. 25, 1993 and Disclosure Document No. 338121 filed Sep. 3, 1993 after producing a load of ground P.E.T. material and having it rejected for having P.V.C. ground in it and being told that if we observed the two materials under ultraviolet black light that there was a slight difference in the two materials color. After viewing the material I noticed that polyethylene terephthalate appeared blue color and polyvinyl chloride appeared an amber/gold color. At that time I began to test for ways to electronically detect the color differences caused by the different materials in ultraviolet black light.

Purposes and Advantages of Invention

The Color Region analyzer can be set to trigger the removal by vacuum at any color value preset within its circuit, This even allows the same product to be graded by different reflected ultra violet stimulated color values. It can see any ultra violet black light stimulated color in its lowest photon energy and allow only a preset color value to be removed by the removal circuit. Thus it allows the detection and removal of P.V.C. material from P.E.T. material and further allows the P.E.T. material to be graded on its color energy and generates data on the test material.

Other filters can be used for other color products as long as the filters that are chosen cause the wanted products light to be blocked or lowered in intensity below the unwanted materials intensity by one of the filters.

The Color region Analyzer uses no chemicals or harmful radiation in its process and creates no hazardous environment for any worker. It runs on 120 volts AC as its supply voltage, and will allow much more recycled material to be reused, instead of going to a land fill.

BRIEF DESCRIPTION OF THE DRAWINGS

FIGS. 3A, 3B, 3C, 3D, 3E, show approximate element placement location in relationship with the cabinet housings.

FIGS. 4A, 48, 4C, 4D and 4E, are other views of the elements to help in understanding these components and their relationship to each other.

Element numbers used in the drawings

Figure 1:
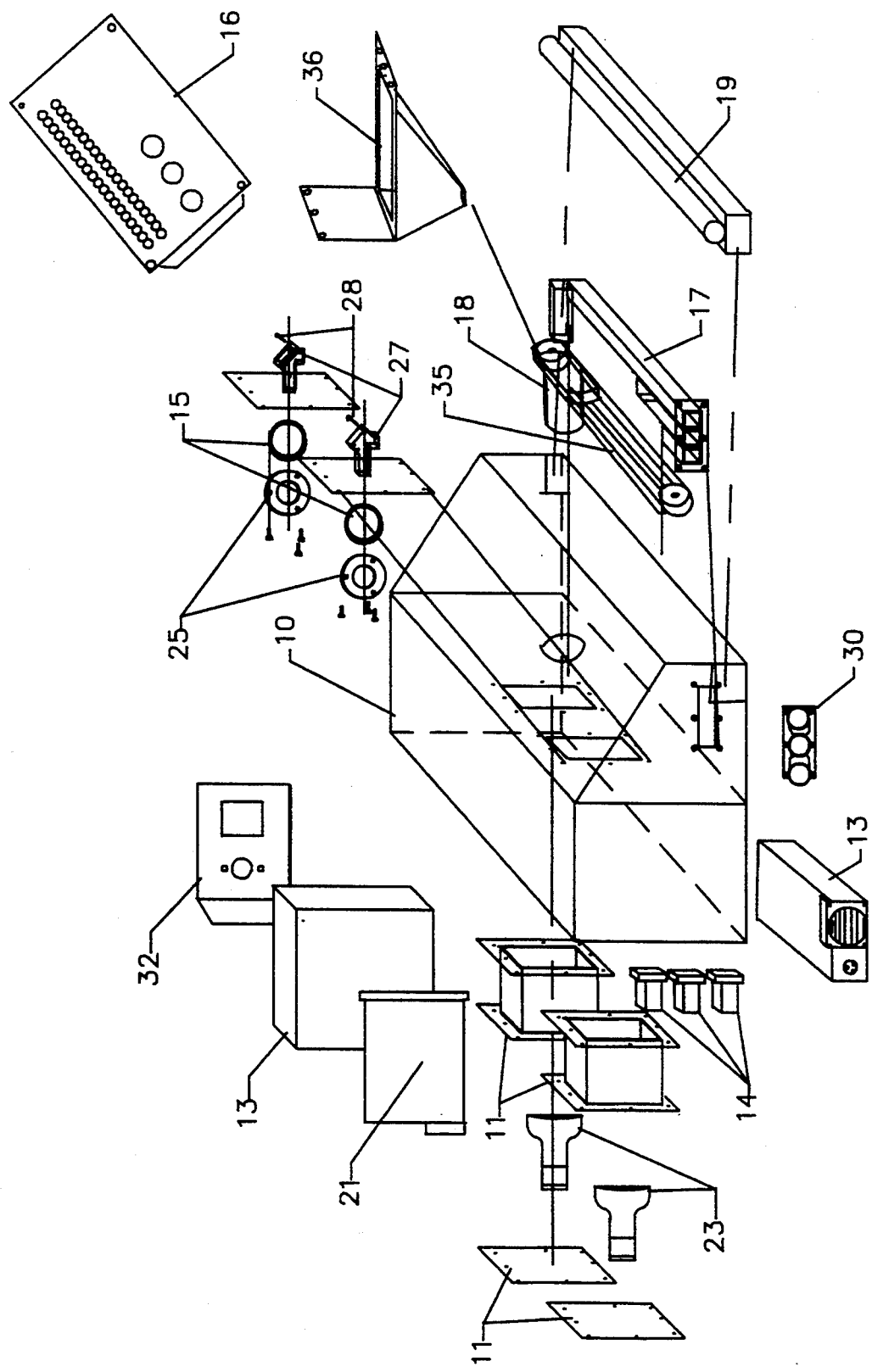
FIG. 1 is an exploded view showing the elements of the Color Region Analyzer.

All element numbers are the same fort all figures and start at the number 10 and continue to number 51.

Element numbers on all drawings indicate the following:

10; cabinet
11; P.M.T. housings
12; vacuum unit
13; power supply, Astec
14; relays
15; filter
16; controls
17; vacuum assembly
18; belt drive
19; ultraviolet black light
20; mirrors
21; logic board
22; vacuum, fines remover
23; photon multiplier tube
24; vacuum valve
25; filter holder
26; gaskets
27; mirror assembly
28; mirror adjustment screws
29; material conveyor belt
30; vacuum output ports
31; power supply, Bertan
32; power supply, Power One
33; vacuum, reject tube
34; vacuum, final tube
35; conveyor belt holder
36; material hopper
37; optocouplers
38; silicone controlled rectifiers
39; operational amplifiers
40; resistor bridge -continued 41; air filter basket
42; shop vacuum port
43; divider plates
44; intake ports
45; vacuum chamber
46; chamber lid
47; filter plate
48; light emitting diode
49; game port series resistor
50; panel switch
51; output to port

DETAILED DESCRIPTION

FIG. 1

FIG. 1 is an exploded view showing the cabinet (10) that houses the photon multiplier tube holders (11), the photon multiplier tube (23), these parts are mounted to the rear side of the partition welded to the center of, as part of the cabinet (10). Mounted to the front of the photon multiplier tubes (11) holders and cabinet partition is the mirror assembly (27), with the filters (15) and filter holders (25). Placed also in the front section of the cabinet (10) is the belt drive (18) and belt holder (35), and the vacuum removal tubes (17), and a 24 inch 20 watt Ultra Violet Black Light (19). Mounted to the angled front of the cabinet (10) is the control panel (16) and the material hopper (36). The power supplies (32,13,31) and the control relays (21) are mounted inside the rear area of the cabinet (10).

FIG. 2

Figure 2:
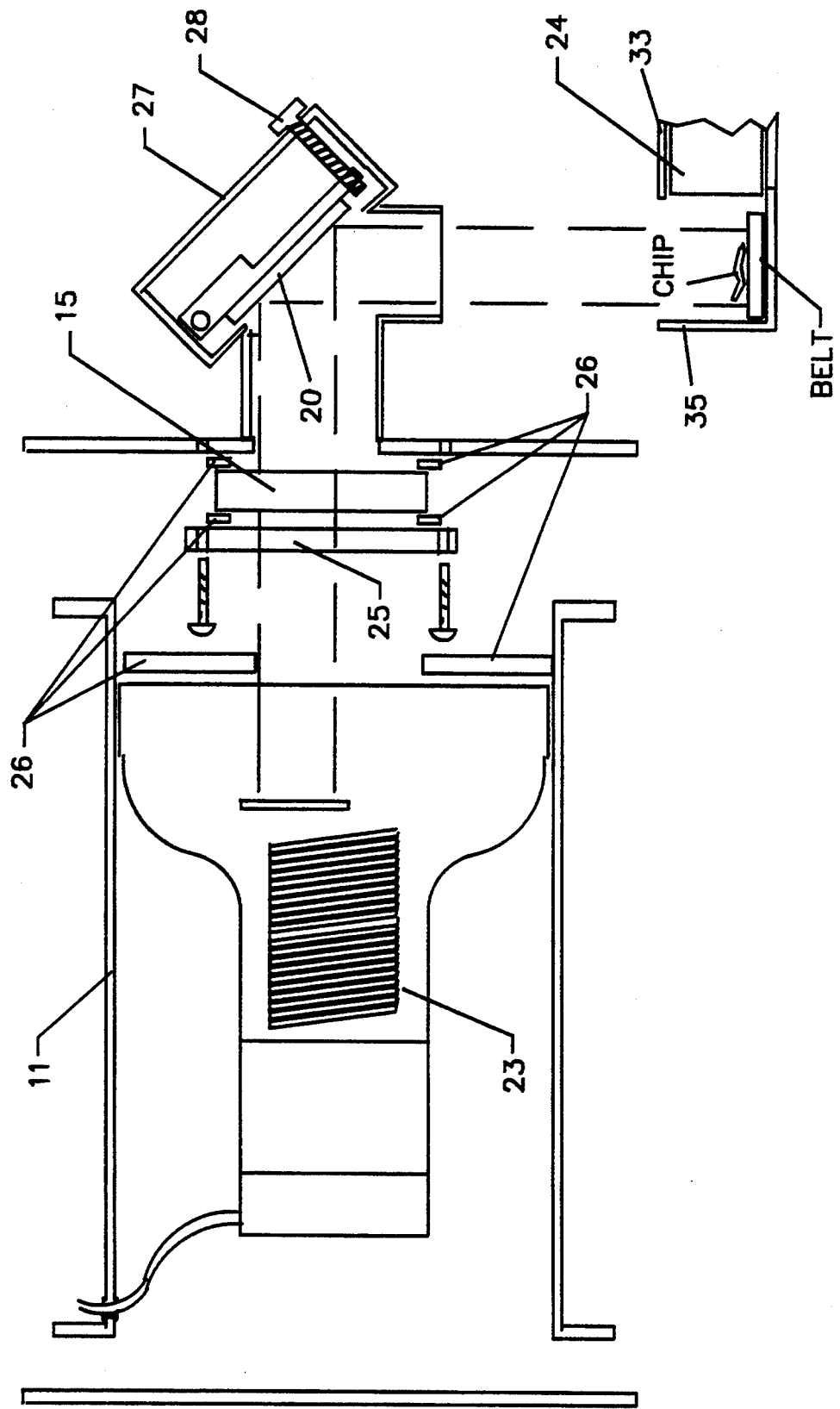
FIG. 2 is a detailed view of the optical elements

FIG. 2 is a exploded, cutaway view of the photon multiplier tubes housing (11) and mirror assembly (27). This Drawing illustrates how ultra violet black light shown as dashed lines is reflected off a chip on the belt held by the belt holder (35) directly in front of the vacuum removal valve (24) mounted at the opening of the vacuum reject tube (33), the reflection from the chip travels upward and on to the mirror assembly (27) and reflected by a mirror (20) with a adjusting screw (28) that adjusts the reflecting angle at 45 degrees more or less to reflect the light from the chip on the belt directly through the filter (15) into the Photon Multiplier Tube (23). A closed cell foam rubber gasket material (26) is Placed around all inner components to seal off and prevent any other light from entering the assembly.

FIG. 3A, 3B, 3C, 3D, 3E

FIG. 3A, 3B, 3C, 3D and 3E illustrates the placement of all formentioned parts location within the cabinet and are referred to by element number in the specification.

FIG. 4A, 4B, 4C, 4D, and 4E

FIG. 4A, 4B, 4C, 4D and 4E illustrates a view of components from the isometric view and are referred to by element number in the specification.

FIG. 5

Figure 5:
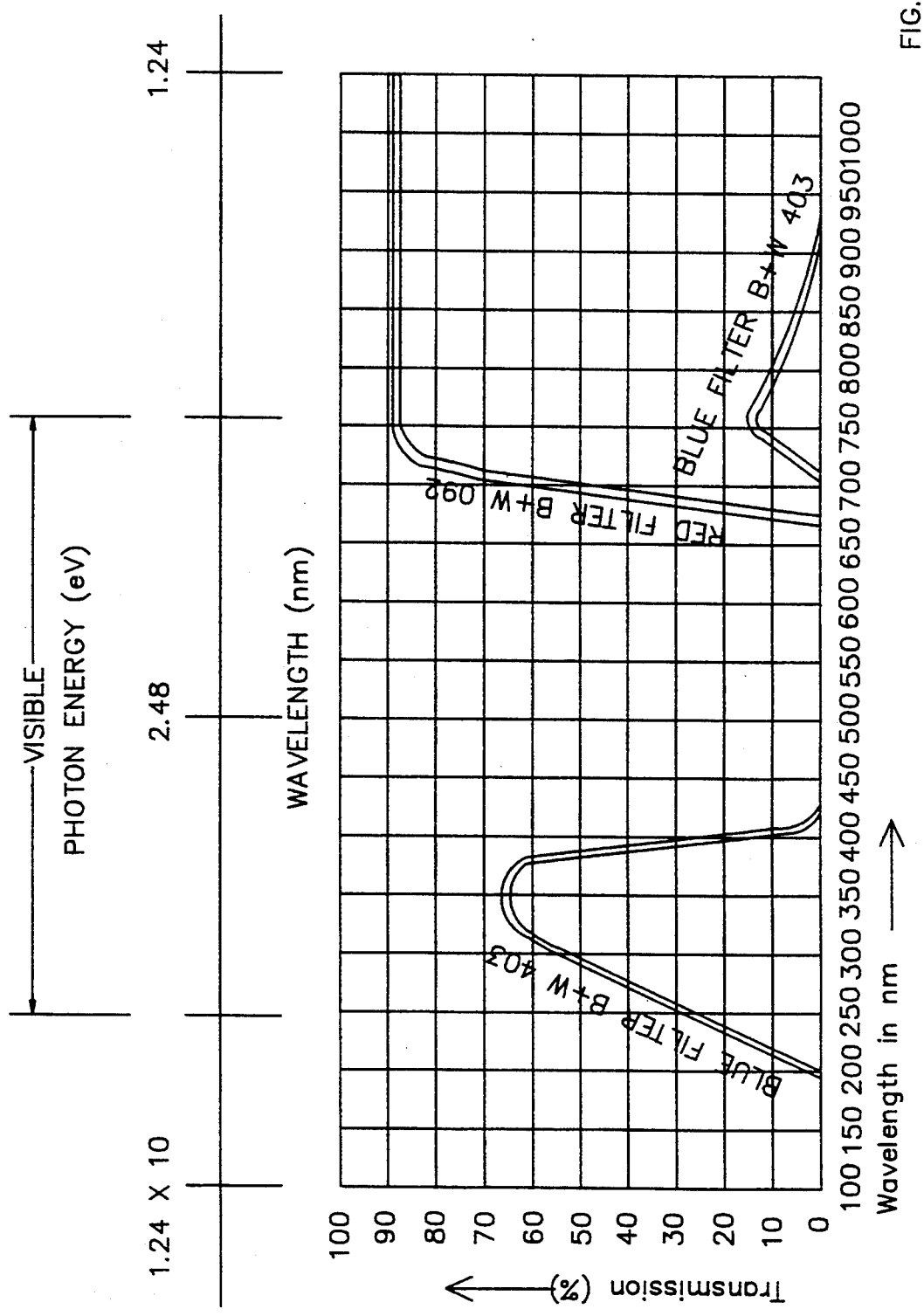
FIG. 5 is a graph that details the filters ability to transmit light as photon energy and the percent of light allowed to pass through each light filter at a given wavelength in nanometers.

FIG. 5 is a graph that illustrates the two filters placed in front of each Photon Multiplier Tube, there is only one filter in front of each photon multiplier tube. The graph shows that the B+W 092 filter mounted in front of one photon multiplier tube only detects: light from 650 nanometer beyond 1000 nanometer in wavelength. The other filter B+W 403 only allows the Photon Multiplier Tube mounted behind it to detect light from 180 nanometer increasing linearly to 350 nanometer then decreasing linearly to 410 nanometer and no detection again until about 710 nanometer in wavelength raising linearly to about 15% at 760 nanometer and decreasing again linearly till about 5930 nano meter. The graph also shows where the Visible light region appears..

FIG. 6

Figure 6:
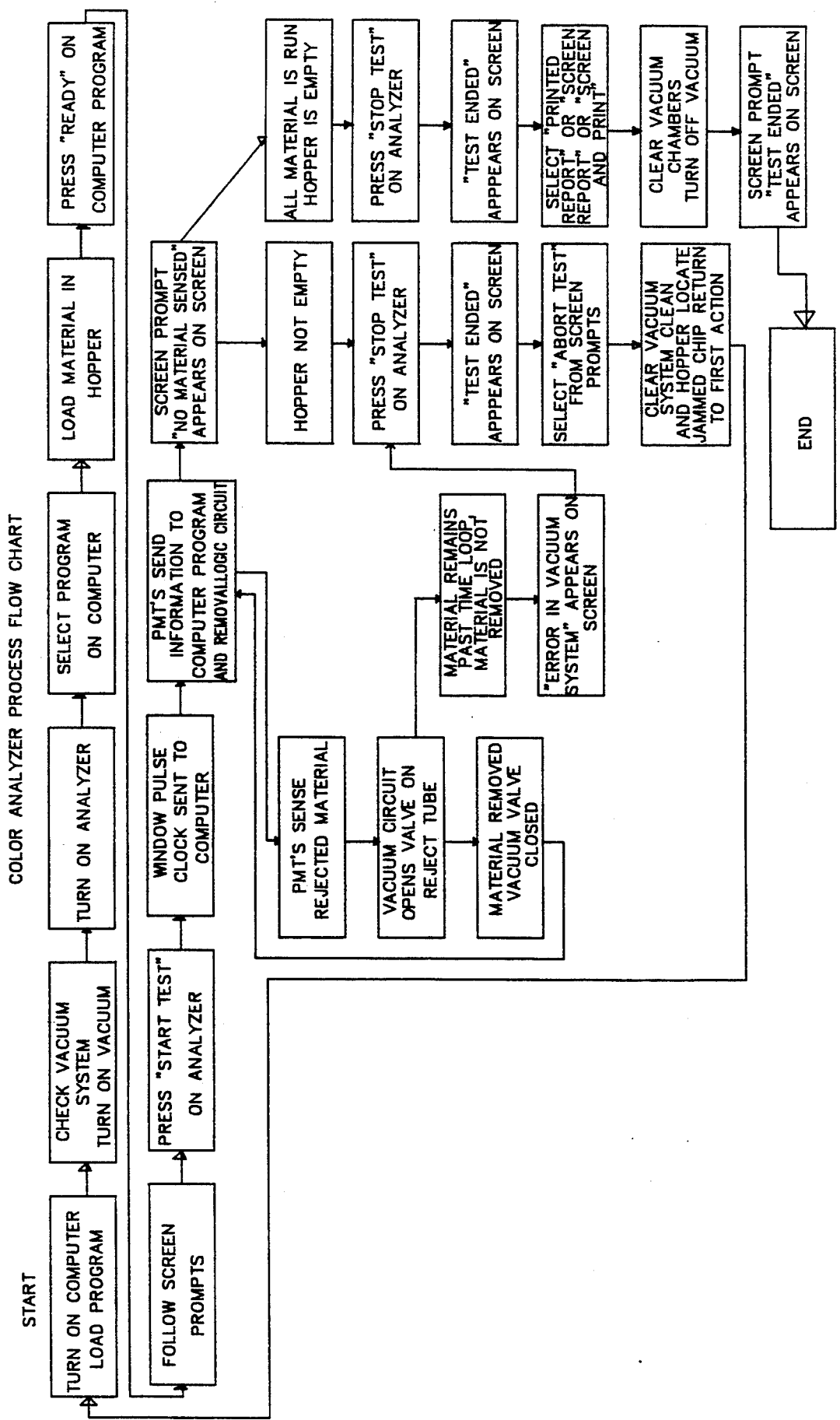
FIG. 6 is a flow chart showing the operational order of a software program working from information transmitted by the invention and the result.

FIG. 6 illustrates the Color Region Analyzers process and operational order, as a block flow chart, showing actions and prompts given by a computer connected by a dual analog game port to the Color Region Analyzer to allow monitoring and reports from the information being sent by the photon multiplier tube, relays and logic board.

FIG. 7

Figure 7:
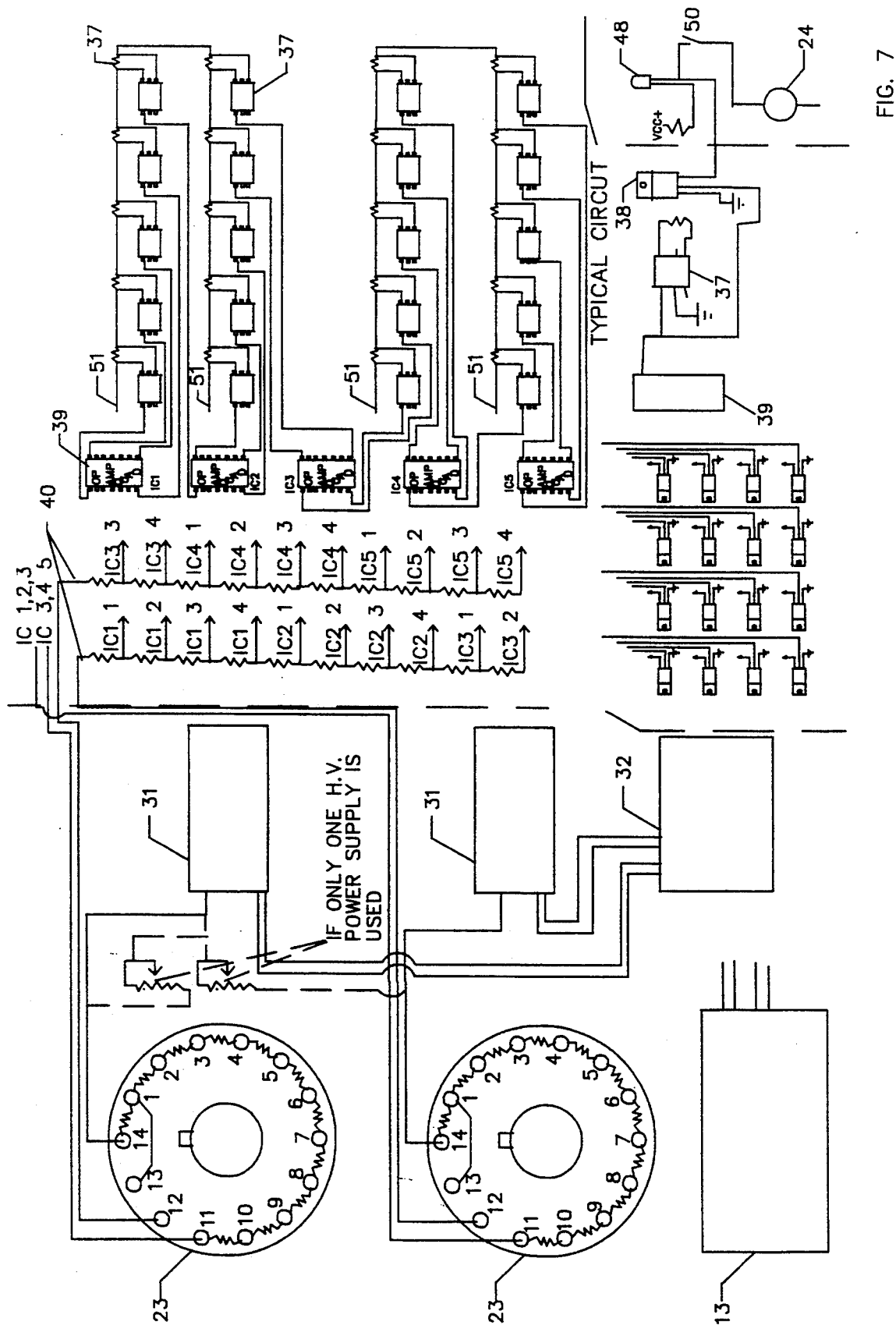
FIG. 7 is a schematic diagram of the logic board to aid in understanding of the electrical logic components.

FIG. 7 is a pictorial schematic of the logic; board showing the connections from the power supplies (31) to the photon multiplier tubes (23). The voltage output of the photon multiplier tubes connected to a resistor bridge containing ten resistors (40) with a connection made between each resistor to a operational amplifiers (39) inverting input and the non inverting input connected to ground state of, the photon multiplier tube (23) within that bridges circuit, then from the outputs of the operational amplifiers to the silicon controlled rectifiers (38) and optocouplers (37). The optocouplers (37) triac outputs are paralleled across a resistor (49) connected in series of ten resistors, connected from the computers game port 5 VDC output (51) to the game ports paddle input (A or B), thus causing the resistor to be null when the optocouplers (37) triac is turned on, thus causing a drop in resistance (49) and increase in voltage to the gameports (51) analog input changing the value of the gameports digital value. Each of the twenty operational amplifiers outputs are also connected to twenty silicon controlled rectifiers (38) gates (only one 9ate is connected to one output) when the output goes high the gate closes and current travels to a light emitting diode (48) and a switch (50), the diode (48) lights and if the switch is turned and passes current to cause the valve (24) to open.

Figure 8:
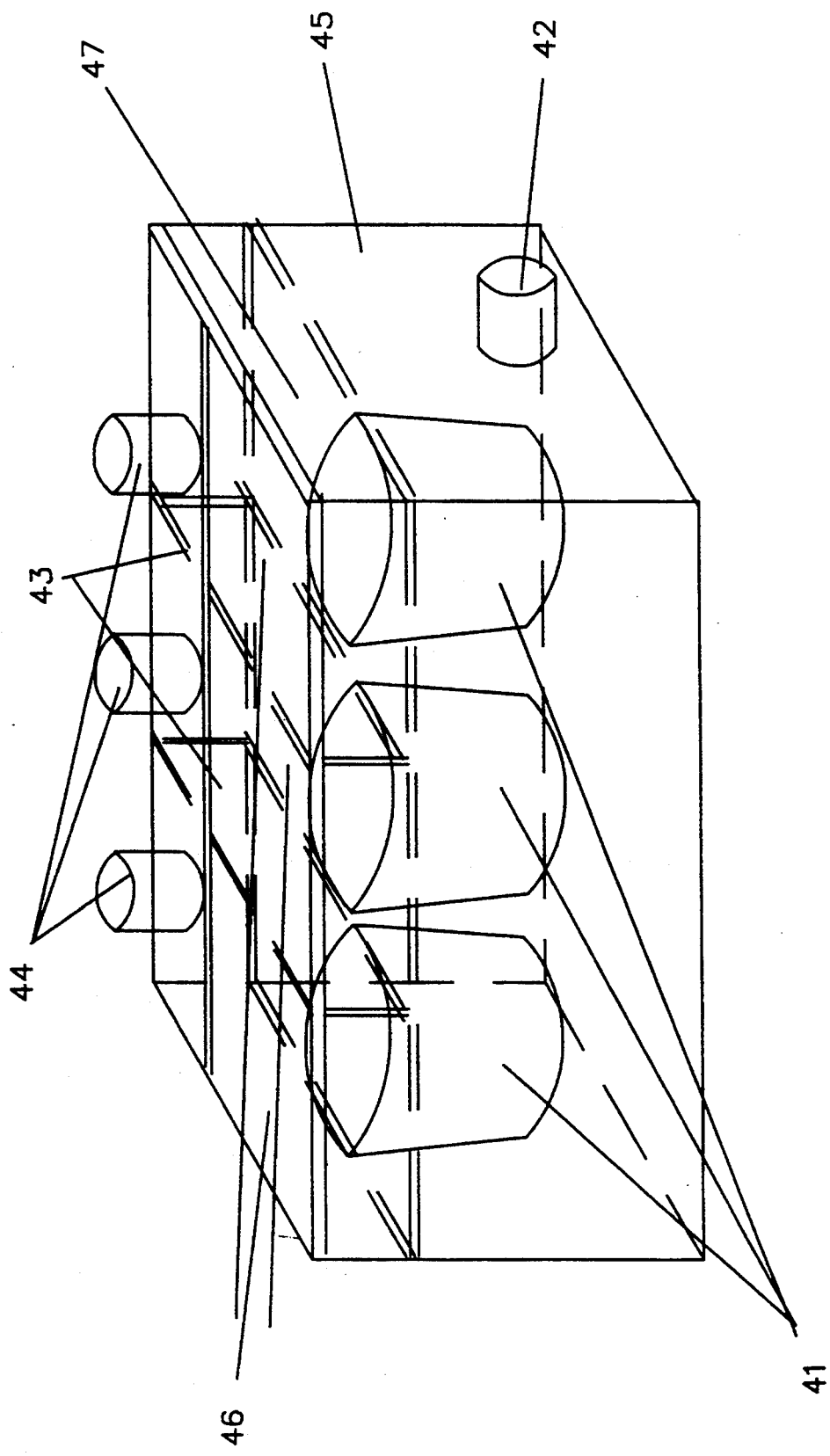
FIG. 8 is a drawing of the vacuum container showing the tubes, chambers and filter baskets.

FIG. 8 illustrates three air filters (41) each with a single input port (44) and separated by a partition (43) between each filter as to not allow any other material to enter but through the single port opening, held in such a way to catch all material passing through the port (44) to be contained within the filter, a cover (46) over each filter so as to allow one filter to be opened at a time, preventing material from accidently being mixed with the other holding cells. A single output (42) is connected to a vacuum source such as a shop vacuum cleaner.

Novel Features

The feature that is novel is the photon multiplier tube fitted with a color blocking filter, (FIG. 2). With the photon multiplier tube and the filter connected in a manner that does not allow any light to enter except through the filter (11) and the filter (15) blocking any other reflected ultra violet black light stimulated color but the color in question (FIG. 5), It is in this novel feature that allows the material in question to be detected, and provides a output current, by allowing the wavelength of color to enter the photon multiplier tube as electro magnetic radiation or photon energy, (FIG. 2), and striking the cathode of the photon multiplier tube (23), causing a linear release of photon energy exponentially within the photon multiplier tube as each plate is struck twice the photon energy is released to the next plate, the final anode plate is multiplied to the tenth power from the photon energy being reflected into the photon multiplier tube, and the photon energy causes a current between the final dynode and anode of the photon multiplier tube that is applied to the balance bridge in the detection circuit, (FIG. 7), connected to the analog to digital converter in the game port and the removal circuit.

Construction

Construction and testing on the Color Region Analyzer for utilizing the filtered Photon multiplier tubes for testing grain probe sized samples taken from 800 to 1000 lb, Gaylord boxes to check for any amounts of P.V.C. in the samples and obtain a report via computer soft ware to later be offered to customers as a quality control report of fitness of the product began on Aug. 11, 1993 and continued until Nov. 3, 1993 when continuous testing proved further improvements were not necessary. All construction was done by myself the Inventor.

Many types of photo detectors were tested using different resistor values and color filters. After trying different circuits and methods of conveying the material it was evident that many methods would work, thus I decided on what would be the least expensive to produce and be the most accurate for the purpose intended.

I did all the software program writing, although with the analog to digital logics type of output it is certain that many software programs and logic applications can be created.

The cabinet and component supports are all made of metal and the entire cabinet front area were the conveyor and ultra violet black light is placed is completely sealed from outside light.

Further testing for other applications

In testing for a) Possible response timing of the operational amplifier circuit,
b) The photon multiplier tubes response to fast moving particles,
c) Encoded spinning mirror to cover wider belts
d) Encoded conveyor belt with location feed back for multi vacuum tube removal
e) Multi layered material
f) Whole bottle detection
g) Other material detection in other light:

The following was found a) The operational amplifier remained stable reading at 10 HHZ
b) When the photon multiplier tube was sampled on a BIOMATION sampling oscilloscope the photon multiplier tube operated at 77 MHZ c) and d) When an encoded spinning mirror was placed at 45 deg, from a 24" wide strip of pre-located mixed particles the location of the P.V.C. chips being reflected into the filtered PMT to the belts location was correct.
e) The red filtered PMT read through 0.5" of clear PET chips and detected a single 0.375" P.V.C. chip placed under the P.E.T. chips
f) In testing whole bottles only one detector fitted with a No. 092 filter under ultra violet black light detected a whole P.V.C. drinking water bottle under 2 P.E.T. pop bottles with labels and base cups, a clear P.V.C. chip 0.375" was detected in the black base cup of a labeled P.E.T. bottle (not through the black base cup)
g) Using the red filtered PMT and low white light it was discovered that the PMT could detect yellow pigmented chips from green pigmented chips Material tested Over 2000 lbs of ground flake material obtained contaminated with different clear P.V.C post consumer bottle products sent from all over the Eastern United States from curb side pick-up were used to test for the ability to detect P.V.C. contamination placed into the P.E.T. flake, all test material was ground in the same grinder as the P.E.T. the material was placed in water and mild dish washing soap separated, (the clear grind sinks to the bottom, the label and base cup floats), the top was skimmed off the clear flake was dried before use. This is basically the same process used to clean the flake in Industry Description of Operation Material is placed in the hopper (36) and the apparatus and personal computer is turned on, all program parameters are selected (FIG. 6), the belt (18) begins to move and material is spread thinly on the 0.75 wide belt, the belt moves into the target area, (intersection of readers shown in FIG. 4A), with ultra violet black light (19) being projected onto the material on target area, the material or chips reflection ultra violet black light color is reflected into the color filtered (15) photon multiplier tubes, (FIG. 2 element 23). If the reflected ultra violet black light color is not blocked by the red filter (15)on the photon multiplier tube then a linear reaction takes place within the photon multiplier tube and a current output is released between the final dynode and the anode, see FIG. 7, if the output has an enough magnitude to create imbalance in the balance bridge then the operational amplifier changes state and places a current on the gate of the silicon controlled rectifier and a light emitting diode and also to the game port on the personal computer by triggering a optocoupler that shorts a resistor causing a higher voltage to flow into the game ports analog to digital converter that the software monitors to compile a data report.

If the corresponding switch on the control panel (16) has been selected, applies current to the vacuum removal valve (24) the circuit remains on until the material creating the response has been removed and is not in the target area.

The Color Region Analyzer separates the material into three filter baskets (FIG. 8), basket one contains very fine (small) particles and any dust and label material. Basket two contains any material rejected by the photon multiplier tubes removal circuit and some P.E.T. that the vacuum removed because it was also present at the removal location at the time the P.V.C. was detected. Basket three, the final vacuum cleans the belt and contains the P.E.T. that passed as not containing P.V.C.

All of the samples were visually rechecked under Ultra Violet Black Light after the test was complete, the material from basket two, the rejected material was found to have only one third of the material to be P.V.C. the rest was P.E.T. the total amount rejected was proportionate to the amount of P.V.C. in total contamination. Thus if there were 20 P.V.C. chips about 60 to 70 total chips were pulled by the vacuum system at the point of rejection the material was then dyed dark blue colored solvent and rinsed and visually separated and melted on copper wire in a flame test to be sure it was P.V.C., P.V.C. will cause the flame to burn bright blue. It was also discovered that some P.V.C. does not appear amber/gold but was rejected.

The material from basket three the "passed" material was tested in the same manner, in earlier tests some P.V.C. was found, a very small amount, but once it was learned that was P.V.C., and its color energy value preset was to be set at for removal, their has been no P.V.C. appearing in the third basket, the material that was allowed to pass by the removal area, in the past 2972 tests.

Novel feature

The manner in which the Color Region Analyzer is able to detect one material color from another, in very low level ultra violet blacklight, is done by Photon multiplier tube fitted with a color wavelength blocking filter, A Photomultiplier tube is one of the most sensitive photodetectors available. A cathode is maintained at a large negative voltage and coated with a photoemissive material and ten dynodes, maintained at successively more positive voltages. The final anode is grounded through a resistor.

A photon of energy enters and strikes the cathode ejecting two photoelectron for each photoelectron striking, these electrons are accelerated striking the first dynode and releasing two photoelectron for each photoelectron striking the first, all these electrons are accelerated to the second dynode where each strikes the surface with sufficient energy to again eject twice the electrons this process is repeated for each dynode until the electrons that reach the anode are greatly multiplied in number, where they constitute a current through the resistor, Thus, the photon multiplier tube has a gain associated with its detection. one single photon striking the cathode may result in a million electrons at the anode.

The spectral response is determined by two factors. The first is the response of the photoemissive material coated on the cathode. The second is the filter through which the electro magnetic radiation must pass thus if the filter does not allow light of a certain wavelength to pass there will be little to no reaction, the wavelength that is allowed to pass will have a reaction, thus by covering both ends of the visible light spectrum a blue chips light is blocked by the red filter thus only the blue filtered photon multiplier tube will have a response to the blue light reflected from the chip, if the material contains red/amber light the blue filtered photon multiplier tube does not respond to the red/amber light energy, but the red filtered photon multiplier tube will. Testing has shown that the closer the color is in spectrum to the blue filtered photon multiplier tube the greater linearly the blue filtered photon multiplier tube detects the material and the less 1lnearly the red filtered photon multiplier tube detects the material.

It should be noted that millions of pounds of plastics are sent to land fills every year, this device will enhance our environment by making it more possible to recycle plastic bottles, because of the certain ramifications that a device capable of detecting and removing contaminates from ground material and further being applied to the removal of contaminates from other recycled plastics, such as contaminates in ground natural milk bottles (H.D.P.E), etc., the application of this Invention will cause more material to be returned to its first intended purpose, thus, saving our natural resources that would have been consumed to create the material that now can be returned to market by recycling and precessing by this device's further applications (multi streams of detection and removal), thus processed material will not go to a land fill.

Keeping in mind that plastics are mostly a product of oil, a great energy savings should also result by the ability to return recycled plastic to the market place and the energy not consumed from manufacturing the amount of material returned for its first intended use.

Although the description contains much anticipation of other devices that this Invention could and will make possible with further application, their are still far more applications that require the ability to analyze the slight or varied differences in reflected or generated light in or out of the visual light spectrum, it is anticipated this device can be used with many other light sources with other types of light filters for monitoring electro magnetic radiation that is generated by chemicals reactions generating photon energy.

I claim:

1. An apparatus for testing and separating mixed ground material which contains at least two types of material ground from containers made of polyethylene terephthalate and polyvinyl chloride free of floatables, comprising:
   means for simultaneously irradiating the ground material with electromagnetic radiation;
   means for reflecting electromagnetic radiation reflected by the material as photon energy;
   a pair of color filter means for receiving the electromagnetic radiation reflected by the reflecting means, each color filter means designed for the extinction of electromagnetic radiation at given nanometer wavelength regions;
   a pair of photodetector means for producing electrical output signals in response to incident electromagnetic radiation, wherein one of the filter means is placed directly in front of each of the photodetector means;
   electronic circuit means connected to the photodetector means for measuring the level of incident electromagnetic radiation;
   removal circuit means connect to the electronic circuit means for removing the material found to be unacceptable as a result of the level of electromagnetic radiation incident on one of the photodetector means and depositing the removed material in a holding chamber; and
   a computer means for monitoring signals from the electronic circuit means and compiling a report on the quality of material based on output signals from the photodetector means representative of the electromagnetic radiation passed through the color filter means.

2. The apparatus of claim 1, wherein each photodetector means has a separate housing and the reflecting means comprises a mirror positioned at substantially 45 degrees with respect to an axis passing through each associated photodetector and filter 3. The apparatus of claim 1, wherein the irradiating means comprises an ultraviolet black light source.

4. The apparatus of claim 1, wherein at least one of the photodetector means is a photomultiplier tube and at least one of the color filter means is a color filter fitted to the photomultiplier tube and designed to block the electromagnetic radiation reflected by polyethylene terephthalate materials, said photomultiplier tube detects electromagnetic radiation reflected by polyvinyl chloride materials as photon energy and produces an electrical output signal to trigger the removal circuit means.

5. The apparatus of claim 1, wherein at least one of the photodetector means is a photomultiplier tube and at least one of the color filter means is a color filter fitted to the photomultiplier tube and designed to block the color generated by polyvinyl chloride materials, said photomultiplier tube detects electromagnetic radiation reflected by good quality polyethlene: terephthalate materials as photon energy.

6. The apparatus of claim 1, further comprising a motor driven mechanical conveyor belt for conveying the material, said belt passing under a funneled hopper with an opening between the hopper and the belt as to allow the material to be deposited onto the conveyor belt and passed in front of the irradiation means and under an optical opening of the filtered photodetector means and a vacuum removal port.

7. The apparatus of claim 1, further comprising:
   housing means comprising a front area sealed from ambient light and containing the irradiating means, a conveyor, a vacuum valve and material removal tubes; and a rear access area closed from the front area and sealed from ambient light for housing circuits, power supplies and the photodetector means;
   a control panel on the front area of the housing means for setting parameters of the removal circuit means; and
   a hopper with an opening in an upper portion thereof to accept ground material and an opening in a lower portion thereof to distribute a layer of the ground material on the conveyor in the front area of the housing means.

* * * * *